(12) United States Patent
Hossainy et al.

(10) Patent No.: US 8,017,140 B2
(45) Date of Patent: Sep. 13, 2011

(54) DRUG-DELIVERY STENT FORMULATIONS FOR RESTENOSIS AND VULNERABLE PLAQUE

(75) Inventors: Syed Faiyaz Ahmed Hossainy, Fremont, CA (US); Gordon Stewart, San Francisco, CA (US); Deborah Kilpatrick, Los Altos, CA (US); Jeffrey Ellis, San Francisco, CA (US); Gene Park, Oakland, CA (US); Gina Zhang, Fremont, CA (US); Paul Consigny, San Jose, CA (US); Yiwen Tang, San Jose, CA (US)

(73) Assignee: Advanced Cardiovascular System, Inc., Santa Clara, CA (US)

( * ) Notice: Subject to any disclaimer, the term of this patent is extended or adjusted under 35 U.S.C. 154(b) by 0 days.

(21) Appl. No.: 11/804,997

(22) Filed: May 21, 2007

(65) Prior Publication Data
US 2007/0269484 A1      Nov. 22, 2007

Related U.S. Application Data

(62) Division of application No. 10/881,540, filed on Jun. 29, 2004, now abandoned.

(51) Int. Cl.
*A61F 13/00* (2006.01)
*A61F 2/00* (2006.01)
*A61K 9/14* (2006.01)

(52) U.S. Cl. ......... 424/422; 424/423; 424/426; 424/486

(58) Field of Classification Search .................. 424/486, 424/422, 426, 423
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,304,767 A | 12/1981 | Heller et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |

(Continued)

FOREIGN PATENT DOCUMENTS

DE           42 24 401           1/1994

(Continued)

OTHER PUBLICATIONS

Tanabe et al, Local Drug Delivery Using coated Stents: New Developments and Future Perspectives, Current Pharmaceutical Design, vol. 10, No. 4, Feb. 2004, pp. 357-367.*

(Continued)

*Primary Examiner* — Blessing Fubara
(74) *Attorney, Agent, or Firm* — Squire, Sanders & Dempsey (US) LLP

(57) ABSTRACT

Drug-delivery stents capable of providing release of two or more drugs such as everolimus and estradiol are provided. The stents can be used for treating a disease such as restenosis and vulnerable plaque.

10 Claims, 2 Drawing Sheets

U.S. PATENT DOCUMENTS

| | | | |
|---|---|---|---|
| 4,882,168 A | 11/1989 | Casey et al. | |
| 4,886,062 A | 12/1989 | Wiktor | |
| 4,931,287 A | 6/1990 | Bae et al. | |
| 4,941,870 A | 7/1990 | Okada et al. | |
| 4,977,901 A | 12/1990 | Ofstead | |
| 5,019,096 A | 5/1991 | Fox, Jr. et al. | |
| 5,100,992 A | 3/1992 | Cohn et al. | |
| 5,112,457 A | 5/1992 | Marchant | |
| 5,133,742 A | 7/1992 | Pinchuk | |
| 5,163,952 A | 11/1992 | Froix | |
| 5,165,919 A | 11/1992 | Sasaki et al. | |
| 5,219,980 A | 6/1993 | Swidler | |
| 5,258,020 A | 11/1993 | Froix | |
| 5,272,012 A | 12/1993 | Opolski | |
| 5,292,516 A | 3/1994 | Viegas et al. | |
| 5,298,260 A | 3/1994 | Viegas et al. | |
| 5,300,295 A | 4/1994 | Viegas et al. | |
| 5,306,501 A | 4/1994 | Viegas et al. | |
| 5,306,786 A | 4/1994 | Moens et al. | |
| 5,328,471 A | 7/1994 | Slepian | |
| 5,330,768 A | 7/1994 | Park et al. | |
| 5,380,299 A | 1/1995 | Fearnot et al. | |
| 5,417,981 A | 5/1995 | Endo et al. | |
| 5,447,724 A | 9/1995 | Helmus et al. | |
| 5,455,040 A | 10/1995 | Marchant | |
| 5,462,990 A | 10/1995 | Hubbell et al. | |
| 5,464,650 A | 11/1995 | Berg et al. | |
| 5,485,496 A | 1/1996 | Lee et al. | |
| 5,516,881 A | 5/1996 | Lee et al. | |
| 5,569,463 A | 10/1996 | Helmus et al. | |
| 5,578,073 A | 11/1996 | Haimovich et al. | |
| 5,581,387 A | 12/1996 | Cahill | |
| 5,584,877 A | 12/1996 | Miyake et al. | |
| 5,605,696 A | 2/1997 | Eury et al. | |
| 5,607,467 A | 3/1997 | Froix | |
| 5,609,629 A | 3/1997 | Fearnot et al. | |
| 5,610,241 A | 3/1997 | Lee et al. | |
| 5,616,338 A | 4/1997 | Fox, Jr. et al. | |
| 5,624,411 A | 4/1997 | Tuch | |
| 5,628,730 A | 5/1997 | Shapland et al. | |
| 5,644,020 A | 7/1997 | Timmermann et al. | |
| 5,649,977 A | 7/1997 | Campbell | |
| 5,658,995 A | 8/1997 | Kohn et al. | |
| 5,667,767 A | 9/1997 | Greff et al. | |
| 5,670,558 A | 9/1997 | Onishi et al. | |
| 5,674,242 A | 10/1997 | Phan et al. | |
| 5,679,400 A | 10/1997 | Tuch | |
| 5,700,286 A | 12/1997 | Tartaglia et al. | |
| 5,702,754 A | 12/1997 | Zhong | |
| 5,711,958 A | 1/1998 | Cohn et al. | |
| 5,716,981 A | 2/1998 | Hunter et al. | |
| 5,721,131 A | 2/1998 | Rudolph et al. | |
| 5,723,219 A | 3/1998 | Kolluri et al. | |
| 5,735,897 A | 4/1998 | Buirge | |
| 5,746,998 A | 5/1998 | Torchilin et al. | |
| 5,759,205 A | 6/1998 | Valentini | |
| 5,776,184 A | 7/1998 | Tuch | |
| 5,783,657 A | 7/1998 | Pavlin et al. | |
| 5,788,979 A | 8/1998 | Alt et al. | |
| 5,800,392 A | 9/1998 | Racchini | |
| 5,820,917 A | 10/1998 | Tuch | |
| 5,824,048 A | 10/1998 | Tuch | |
| 5,824,049 A | 10/1998 | Ragheb et al. | |
| 5,830,178 A | 11/1998 | Jones et al. | |
| 5,837,008 A | 11/1998 | Berg et al. | |
| 5,837,313 A | 11/1998 | Ding et al. | |
| 5,849,859 A | 12/1998 | Acemoglu | |
| 5,851,508 A | 12/1998 | Greff et al. | |
| 5,854,376 A | 12/1998 | Higashi | |
| 5,858,746 A | 1/1999 | Hubbell et al. | |
| 5,861,387 A | 1/1999 | Labrie et al. | |
| 5,865,814 A | 2/1999 | Tuch | |
| 5,869,127 A | 2/1999 | Zhong | |
| 5,873,904 A | 2/1999 | Ragheb et al. | |
| 5,876,433 A | 3/1999 | Lunn | |
| 5,877,224 A | 3/1999 | Brocchini et al. | |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | |
| 5,932,299 A | 8/1999 | Katoot | |
| 5,955,509 A | 9/1999 | Webber et al. | |
| 5,958,385 A | 9/1999 | Tondeur et al. | |
| 5,962,138 A | 10/1999 | Kolluri et al. | |
| 5,971,954 A | 10/1999 | Conway et al. | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,011,125 A | 1/2000 | Lohmeijer et al. | |
| 6,015,541 A | 1/2000 | Greff et al. | |
| 6,033,582 A | 3/2000 | Lee et al. | |
| 6,034,204 A | 3/2000 | Mohr et al. | |
| 6,042,875 A | 3/2000 | Ding et al. | |
| 6,051,576 A | 4/2000 | Ashton et al. | |
| 6,051,648 A | 4/2000 | Rhee et al. | |
| 6,054,553 A | 4/2000 | Groth et al. | |
| 6,056,993 A | 5/2000 | Leidner et al. | |
| 6,060,451 A | 5/2000 | DiMaio et al. | |
| 6,060,518 A | 5/2000 | Kabanov et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,110,483 A | 8/2000 | Whitbourne et al. | |
| 6,113,629 A | 9/2000 | Ken | |
| 6,120,491 A | 9/2000 | Kohn et al. | |
| 6,120,536 A | 9/2000 | Ding et al. | |
| 6,120,788 A | 9/2000 | Barrows | |
| 6,120,904 A | 9/2000 | Hostettler et al. | |
| 6,121,027 A | 9/2000 | Clapper et al. | |
| 6,129,761 A | 10/2000 | Hubbell | |
| 6,136,333 A | 10/2000 | Cohn et al. | |
| 6,143,354 A | 11/2000 | Koulik et al. | |
| 6,153,252 A * | 11/2000 | Hossainy et al. | 427/2.3 |
| 6,159,978 A | 12/2000 | Myers et al. | |
| 6,165,212 A | 12/2000 | Dereume et al. | |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | |
| 6,211,249 B1 | 4/2001 | Cohn et al. | |
| 6,214,901 B1 | 4/2001 | Chudzik et al. | |
| 6,231,600 B1 | 5/2001 | Zhong | |
| 6,240,616 B1 | 6/2001 | Yan | |
| 6,245,753 B1 | 6/2001 | Byun et al. | |
| 6,245,760 B1 | 6/2001 | He et al. | |
| 6,248,129 B1 | 6/2001 | Froix | |
| 6,251,136 B1 | 6/2001 | Guruwaiya et al. | |
| 6,254,632 B1 | 7/2001 | Wu et al. | |
| 6,258,121 B1 | 7/2001 | Yang et al. | |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,273,913 B1 | 8/2001 | Wright et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,299,604 B1 | 10/2001 | Ragheb et al. | |
| 6,306,176 B1 | 10/2001 | Whitbourne | |
| 6,331,313 B1 | 12/2001 | Wong et al. | |
| 6,335,029 B1 | 1/2002 | Kamath et al. | |
| 6,344,035 B1 | 2/2002 | Chudzik et al. | |
| 6,346,110 B2 | 2/2002 | Wu | |
| 6,358,556 B1 | 3/2002 | Ding et al. | |
| 6,379,381 B1 | 4/2002 | Hossainy et al. | |
| 6,383,215 B1 | 5/2002 | Sass | |
| 6,387,379 B1 | 5/2002 | Goldberg et al. | |
| 6,395,326 B1 | 5/2002 | Castro et al. | |
| 6,419,692 B1 | 7/2002 | Yang et al. | |
| 6,451,373 B1 | 9/2002 | Hossainy et al. | |
| 6,471,979 B2 * | 10/2002 | New et al. | 424/422 |

| | | | |
|---|---|---|---|
| 6,482,834 B2 | 11/2002 | Spada et al. | |
| 6,494,862 B1 | 12/2002 | Ray et al. | |
| 6,503,538 B1 | 1/2003 | Chu et al. | |
| 6,503,556 B2 | 1/2003 | Harish et al. | |
| 6,503,954 B1 | 1/2003 | Bhat et al. | |
| 6,506,437 B1 | 1/2003 | Harish et al. | |
| 6,524,347 B1 | 2/2003 | Myers et al. | |
| 6,527,801 B1 | 3/2003 | Dutta | |
| 6,527,863 B1 | 3/2003 | Pacetti et al. | |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | |
| 6,544,223 B1 | 4/2003 | Kokish | |
| 6,544,543 B1 | 4/2003 | Mandrusov et al. | |
| 6,544,582 B1 | 4/2003 | Yoe | |
| 6,555,157 B1 | 4/2003 | Hossainy | |
| 6,558,733 B1 | 5/2003 | Hossainy et al. | |
| 6,565,659 B1 | 5/2003 | Pacetti et al. | |
| 6,572,644 B1 | 6/2003 | Moein | |
| 6,585,755 B2 | 7/2003 | Jackson et al. | |
| 6,585,765 B1 | 7/2003 | Hossainy et al. | |
| 6,585,926 B1 | 7/2003 | Mirzaee | |
| 6,605,154 B1 | 8/2003 | Villareal | |
| 6,616,765 B1 | 9/2003 | Hossaony et al. | |
| 6,623,448 B2 | 9/2003 | Slater | |
| 6,625,486 B2 | 9/2003 | Lundkvist et al. | |
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,695,920 B1 | 2/2004 | Pacetti et al. | |
| 6,703,040 B2 | 3/2004 | Katsarava et al. | |
| 6,706,013 B1 | 3/2004 | Bhat et al. | |
| 6,709,514 B1 | 3/2004 | Hossainy | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |
| 6,733,768 B2 | 5/2004 | Hossainy et al. | |
| 6,740,040 B1 | 5/2004 | Mandrusov et al. | |
| 6,743,462 B1 | 6/2004 | Pacetti | |
| 6,749,626 B1 | 6/2004 | Bhat et al. | |
| 6,753,071 B1 | 6/2004 | Pacetti et al. | |
| 6,758,859 B1 | 7/2004 | Dang et al. | |
| 6,759,054 B2 | 7/2004 | Chen et al. | |
| 6,764,505 B1 | 7/2004 | Hossainy et al. | |
| 6,908,624 B2 * | 6/2005 | Hossainy et al. | 424/424 |
| 2001/0007083 A1 | 7/2001 | Roorda | |
| 2001/0014717 A1 | 8/2001 | Hossainy et al. | |
| 2001/0018469 A1 | 8/2001 | Chen et al. | |
| 2001/0020011 A1 | 9/2001 | Mathiowitz et al. | |
| 2001/0029351 A1 | 10/2001 | Falotico et al. | |
| 2001/0037145 A1 | 11/2001 | Guruwaiya et al. | |
| 2001/0051608 A1 | 12/2001 | Mathiowitz et al. | |
| 2002/0005206 A1 | 1/2002 | Falotico et al. | |
| 2002/0007213 A1 | 1/2002 | Falotico et al. | |
| 2002/0007214 A1 | 1/2002 | Falotico | |
| 2002/0007215 A1 | 1/2002 | Falotico et al. | |
| 2002/0009604 A1 | 1/2002 | Zamora et al. | |
| 2002/0016625 A1 | 2/2002 | Falotico et al. | |
| 2002/0032414 A1 | 3/2002 | Ragheb et al. | |
| 2002/0032434 A1 | 3/2002 | Chudzik et al. | |
| 2002/0051730 A1 | 5/2002 | Bodnar et al. | |
| 2002/0062147 A1 | 5/2002 | Yang | |
| 2002/0071822 A1 | 6/2002 | Uhrich | |
| 2002/0077693 A1 | 6/2002 | Barclay et al. | |
| 2002/0082679 A1 | 6/2002 | Sirhan et al. | |
| 2002/0087123 A1 | 7/2002 | Hossainy et al. | |
| 2002/0091433 A1 | 7/2002 | Ding et al. | |
| 2002/0094440 A1 | 7/2002 | Llanos et al. | |
| 2002/0111590 A1 | 8/2002 | Davila et al. | |
| 2002/0120326 A1 | 8/2002 | Michal | |
| 2002/0123801 A1 | 9/2002 | Pacetti et al. | |
| 2002/0142039 A1 | 10/2002 | Claude | |
| 2002/0155212 A1 | 10/2002 | Hossainy | |
| 2002/0165608 A1 | 11/2002 | Llanos et al. | |
| 2002/0176849 A1 | 11/2002 | Slepian | |
| 2002/0183581 A1 | 12/2002 | Yoe et al. | |
| 2002/0188037 A1 | 12/2002 | Chudzik et al. | |
| 2002/0188277 A1 | 12/2002 | Roorda et al. | |
| 2003/0004141 A1 | 1/2003 | Brown | |
| 2003/0028243 A1 | 2/2003 | Bates et al. | |
| 2003/0028244 A1 | 2/2003 | Bates et al. | |
| 2003/0031780 A1 | 2/2003 | Chudzik et al. | |
| 2003/0032767 A1 | 2/2003 | Tada et al. | |
| 2003/0036794 A1 | 2/2003 | Ragheb et al. | |
| 2003/0039689 A1 | 2/2003 | Chen et al. | |
| 2003/0040712 A1 | 2/2003 | Ray et al. | |
| 2003/0040790 A1 | 2/2003 | Furst | |
| 2003/0059520 A1 | 3/2003 | Chen et al. | |
| 2003/0060877 A1 | 3/2003 | Falotico et al. | |
| 2003/0065377 A1 | 4/2003 | Davila et al. | |
| 2003/0068355 A1 * | 4/2003 | Shanley et al. | 424/426 |
| 2003/0072868 A1 | 4/2003 | Harish et al. | |
| 2003/0073961 A1 | 4/2003 | Happ | |
| 2003/0083646 A1 | 5/2003 | Sirhan et al. | |
| 2003/0083739 A1 | 5/2003 | Cafferata | |
| 2003/0097088 A1 | 5/2003 | Pacetti | |
| 2003/0097173 A1 | 5/2003 | Dutta | |
| 2003/0099712 A1 | 5/2003 | Jayaraman | |
| 2003/0105236 A1 | 6/2003 | Dutta | |
| 2003/0113439 A1 | 6/2003 | Pacetti et al. | |
| 2003/0125800 A1 * | 7/2003 | Shulze et al. | 623/1.15 |
| 2003/0150380 A1 | 8/2003 | Yoe | |
| 2003/0157241 A1 | 8/2003 | Hossainy et al. | |
| 2003/0158517 A1 | 8/2003 | Kokish | |
| 2003/0190406 A1 | 10/2003 | Hossainy et al. | |
| 2003/0207020 A1 | 11/2003 | Villareal | |
| 2003/0211230 A1 | 11/2003 | Pacetti et al. | |
| 2004/0018296 A1 | 1/2004 | Castro et al. | |
| 2004/0029952 A1 | 2/2004 | Chen et al. | |
| 2004/0037886 A1 * | 2/2004 | Hsu | 424/486 |
| 2004/0047978 A1 | 3/2004 | Hossainy et al. | |
| 2004/0047980 A1 | 3/2004 | Pacetti et al. | |
| 2004/0052858 A1 | 3/2004 | Wu et al. | |
| 2004/0052859 A1 | 3/2004 | Wu et al. | |
| 2004/0054104 A1 | 3/2004 | Pacetti | |
| 2004/0060508 A1 | 4/2004 | Pacetti et al. | |
| 2004/0062853 A1 | 4/2004 | Pacetti et al. | |
| 2004/0063805 A1 | 4/2004 | Pacetti et al. | |
| 2004/0071861 A1 | 4/2004 | Mandrusov et al. | |
| 2004/0072922 A1 | 4/2004 | Hossainy et al. | |
| 2004/0073298 A1 | 4/2004 | Hossainy | |
| 2004/0086542 A1 | 5/2004 | Hossainy et al. | |
| 2004/0086550 A1 | 5/2004 | Roorda et al. | |
| 2004/0096504 A1 | 5/2004 | Michal | |
| 2004/0098117 A1 | 5/2004 | Hossainy et al. | |
| 2004/0143322 A1 * | 7/2004 | Litvack et al. | 623/1.42 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |

| | | |
|---|---|---|
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/017892 | 3/2004 |

OTHER PUBLICATIONS

Date of the article is included in a different document Tanabe et al is provided as an evidence.*
Wieneke et al. ("Monthly Focus: Cardiovascular & Renal Therapeutic potential of active stent coating," in Investig. Drugs (2003) 12 (5), pp. 771-779).*
Tanabe et al. ("Local drug Delivery Using Coated Stents: New Developments and Future Perspectives," in Current Pharmaceutical Design, 2004, vol. 10, No. 4, pp. 357-367).*
Smith et al. ("Antiproliferative Coatings for the treatment of Coronary Heart Disease: What Are the Targets and which are the tools?" in Journal of Interventional Cardiology, vol. 16, No. 6, 2003, pp. 475-483).*
Aggarwal et al. ("Stent-based immunosuppressive therapies for the prevention of restenosis," in Cardiovascular Radiation Medicine, vol. 4, Issue 2, Apr.-Jun. 2003, pp. 98-107).*
Waksman ("Drug-eluting stents from bench to bed," in Cardiovascular Radiation Medicine 3 (2002) 226-241).*
Michael J. B. Kurtryk, Cardiology Rounds, Drug-eluting stent for the treatment of coronary artery disease Part 4: New results from clinical trials and future direction, Dec. 2003.*
U.S. Appl. No. 10/630,250, filed Jul. 30, 2002, Pacetti et al.
U.S. Appl. No. 10/718,278, filed Nov. 19, 2003, Hossainy et al.
U.S. Appl. No. 10/719,516, filed Nov. 21, 2003, Tang et al.
U.S. Appl. No. 10/738,704, filed Dec. 16, 2003, Pacetti et al.
U.S. Appl. No. 10/741,214, filed Dec. 19, 2003, Pacetti et al.
U.S. Appl. No. 10/750,139, filed Dec. 30, 2003, Desnoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/835,656, filed Apr. 30, 2004, Tang et al.
U.S. Appl. No. 10/855,294, filed May 26, 2004, Pacetti et al.
International Search Report for PCT/US2005/023006, filed Jun. 27, 2005, mailed Oct. 24, 2005, 14 pgs.
Anonymous, *Cardiologists Draw-Up The Dream Stent*, Clinica 710:15 (Jun. 17, 1996), http://www.dialogweb.com/cgi/document?reg=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
Chung et al., *Inner core segment design for drug delivery control of thermo-responsive polymeric micelles*, Journal of Controlled Release 65:93-103 (2000).
De Lezo et al., *Intracoronary Ultrasound Assessment of Directional Coronary Atherectomy: Immediate and Follow-Up Findings*, JACC vol. 21, No. 2, (1993) pp. 298-307.
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Kutryk, Cardiology Rounds, Drug-eluting stents for the treatment of coronary artery disease part 4: New results from clinical trials and future direction, available at http://www.cardiologyrounds.ca/crus/cardiocdnen_1203.pdf, Dec. 2003.
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Moreno et al., *Macrophage Infiltration Predicts Restenosis After Coronary Intervention in Patients with Unstable Angina*, Circulation, vol. 94, No. 12, (1996) pp. 3098-3102.

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Oikawa et al., *Mechanisms of Acute Gain and Late Lumen Loss After Atherectomy in Different Preintervention Arterial Remodeling Patterns*, The Am. J. of Cardilogy, vol. 89, (2002) pp. 505-510.

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Scully et al., *Effect of a heparan sulphate with high affinity for antithrombin III upon inactivation of thrombin and coagulaton Factor Xa*, Biochem J. 262, (1989) pp. 651-658.

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Virmani et al., *Lessons From Sudden Coronary Death a Comprehensive Morphological Classification Scheme for Atherosclerotic Lesions*, Arterioscler Thromb Vasc Biol. (2000) pp. 1262-1275.

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

DRUG-DELIVERY STENT FORMULATIONS FOR RESTENOSIS AND VULNERABLE PLAQUE

CROSS-REFERENCE TO RELATED APPLICATION

This is a divisional application of U.S. application Ser. No. 10/881,540, filed on Jun. 29, 2004 now abandoned, the teaching of which is incorporated herein by reference in its entirety.

BACKGROUND OF THE INVENTION

1. Field of the Invention

This invention relates to drug combinations, formulations, and methods of application for the treatment or prevention of vascular disorder such as restenosis and/or vulnerable plaque. More superficially, the invention relates to application of everolimus and estradiol such as by a stent.

2. Description of the Background

Plaques have been associated with stenosis and restenosis. While treatments of plaque-induced stenosis and restenosis have advanced significantly over the last few decades, the morbidity and mortality associated with vascular plaques have remained significant. Recent work suggests that plaques may generally fall into one of two different general types: standard stenotic plaques and vulnerable plaques. Stenotic plaque, which is sometimes referred to as thrombosis-resistant plaque, can generally be treated effectively by the known intravascular lumen opening techniques. Although the stenosis the plaques induce may require treatment, these atherosclerotic plaques themselves are often a benign and effectively treatable disease.

Unfortunately, as plaque matures, narrowing of a blood vessel by a proliferation of smooth muscle cells, matrix synthesis, and lipid accumulation may result in formation of a plaque which is quite different than a standard stenotic plaque. Such atherosclerotic plaque becomes thrombosis-prone, and can be highly dangerous. This thrombosis-prone or vulnerable plaque may be a frequent cause of an acute coronary syndrome.

Coronary heart disease is generally thought to be caused by the narrowing of coronary arteries by atherosclerosis, the buildup of fatty deposits in the lining of the arteries. The process that may lead to atherosclerosis begins with the accumulation of excess fats and cholesterol in the blood. These substances infiltrate the lining of arteries, gradually increasing in size to form deposits commonly referred to as plaque or atherosclerotic occlusions. Plaques narrow the arterial lumen and impede blood flow. Blood cells may collect around the plaque, eventually creating a blood clot that may block the artery completely.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect vulnerable plaque growth into the arterial wall. After death, an autopsy can reveal the plaque congested in arterial wall that could not have been seen otherwise with currently available medical technology.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, whose reduced concentration combined with macrophage derived enzyme degradations can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of the unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

While the known procedures for treating plaque have gained wide acceptance and shown good efficacy for treatment of standard stenotic plaques, they may be ineffective (and possibly dangerous) when thrombotic conditions are superimposed on atherosclerotic plaques. Specifically, mechanical stresses caused by primary treatments like percutaneous transluminal coronary intervention (PTCI), such as stenting, may actually trigger release of fluids and/or solids from a vulnerable plaque into the blood stream, thereby potentially causing a coronary thrombotic occlusion. For example, rupture of the fibrous cap that overlies the thrombogenic necrotic core is presently believed to play an important role in acute ischemic events, such as stroke, transient ischemic attack, myocardial infarction, and unstable angina (Virmani R, et al. Arterioscler Thromb Vasc Biol. 20: 1262-1275 (2000)). There is evidence that fibrous cap can be ruptured during stent deployment. Human data from various sources have indicated that lipid rich and/or positively remodeled and/or echolucent lesions in sysmptomatic coronary atherosclerosis have higher likelihood for restenosis (See, for example, J. Am. Coll. Cardiol. 21(2):298-307 (1993); Am. J. Cardiol. 89(5):505 (2002); Circ. 94(12):3098-102 (1996)). Therefore, there is a need for stabilization of thin fibrous cap by building-up additional fibrous mass in a controlled manner without triggering occlusive restenosis.

The drug formulations and delivery methods of the present invention address issues of restenosis, vulnerable plaque and other disorders.

SUMMARY OF THE INVENTION

Described herein is a coating formulation for controlled release of two or more drugs for treating a medical condition. The coating is capable of a variety of combinations of release of the two or more drugs.

The release profiles of the drugs are tailored to meet various therapeutic needs. Therapeutic intervention of a drug may vary as a function of time because the mechanistic target of the drug may be a function of time. For example, anti-proliferative drugs may need to be released between 5 days to 30 days after implantation, and anti-inflammatory or antiplatelet drugs may need to be delivered acutely during the implantation procedure followed by a sustained release up to 2 months after implantation. Antimigratory drugs may need to be released within 1-4 weeks. The coating described herein, in one embodiment, is capable of providing a pulse or fast release of a first drug followed by a sustained release the first drug. The coating can further provide a fast release and/or followed by a sustained release of a second drug over a defined period.

A stent having a coating formulation defined herein can be used to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

DETAILED DESCRIPTION

Figure 1:
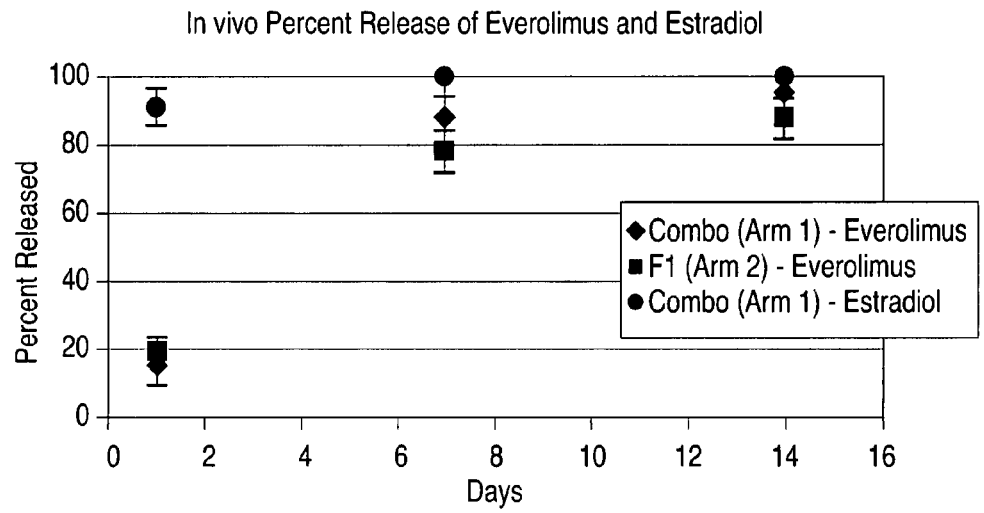
FIG. 1 shows the in vivo percent release of everolimus and 17-beta-estradiol, further showing that it is possible to have a controlled release of everolimus and 17-beta-estradiol simultaneously (designated as "Combo"). For comparison, stents that elute only everolimus were formed to have a coating that includes an EVAL primer and a layer that includes 1:3 everolimus to EVAL polymer ratio (total solid 284 µg) (designated as "F1").

In one embodiment a drug release profile or drug formulation is disclosed for the treatment of vascular disorder or related disorder. More specifically, the vascular disorder is restenosis and/or vulnerable plaque. The term "treatment" includes prevention, reduction, delay or elimination of the referred to disorder. In some embodiments, treatment also includes repairing damage caused by the disorder or the mechanical intervention, e.g., stenting. The mode of deliver of any one or the combination of the drugs can be local or systemic. Local administration can be by a stent (e.g., coated stent or biodegradable or bioabsorbable stent), a drug delivery particle or other known methods of local drug delivery. Systemic administration can be accomplished orally or parenterally, including intravascularly. For example, in one embodiment, a first drug can be delivered by a stent and the other by a catheter at the site of treatment. The delivery can be simultaneous or in sequence. In one embodiment, one of the drugs can be delivered before the other while there is some or a significant overlap between the deliveries of both. Preferably, the drug treatment is via a stent.

Therapeutic intervention of a drug may vary as a function of time because the mechanistic target of the drug may be a function of time. For example, anti-proliferative drugs may need to be released within a period of time between 3 days to 30 days after implantation, and anti-inflammatory or anti-platelet drugs may need to be delivered acutely during the implantation procedure followed by a sustained release up to 2 months after implantation. Antimigratory drugs may need to be released within 1-4 weeks.

For stent applications, the release profiles of the drugs can be tailored by using different types of coating material in mixed, bonded, or layered format; modifying the coating material; or positioning of the coating layers on the stents. Coating layers can include any combinations of a primer layer, a reservoir layer, a topcoat layer and a finishing coat layer. Any of the layers can include a biocompatible polymer as described below. For example, any of the layers, such as the barrier polymer can be a biocompatible polymer capable of controlled release of a drug by virtue of very low equilibrium water uptake. The term "very low equilibrium water uptake" can be defined as having a water permeability of less than about 1% by weight. Generally, a barrier formed of a hydrophobic biocompatible polymer would have a very low equilibrium water uptake. Polymers fall within this category include, for example, polystyrene, poly(butyl methacrylate) (PBMA), poly(D,L-lactic acid) (PDLLA), poly(L-lactic acid) (PLLA) or poly(D,L-lactic acid-co-glycolic acid) (PDLLAGA). In one embodiment, a layer, such as the barrier polymer, can be formed of a bioabsorable polymer such as polycaprolactone (PCL), poly(ester amides) (PEA), polyhydroxyalkanoate (PHA), or poly(3-hydroxybutyrate) (PHB), vinylidene fluoride based homopolymers such as polyvinylidene fluoride (PVDF) and copolymers such as poly(vinylidene fluoride-co-hexafluoropropylene) (PVDF-co-HFP). Vinylidene fluoride based polymers are commercially available under the trade name Kynar™ and Solef™.

In one embodiment, the coating can have any one or combination of a pulse, burst or sustained release profile. For example, the coating can be made to have a pulse or burst release of a drug, followed by a sustained release of the same drug. The drug can be a bioactive agent as defined below. Preferably, the drug is an anti-proliferative 40-O-(2-hydroxy)ethyl-rapamycin (known by the trade name of everolimus, available from Novartis as Certican™), estradiol such as 17-beta-estradiol, other estrogen receptors, anti-proliferative drugs, immunosuppresant drugs, anti-inflammatory drugs, anti platelet drugs, antimigratory drugs, anti-thrombotic drugs, drugs that regress plaque such as high density lipoprotein (HDL)-mimetics, agents that promotes endothelial cell growth, prohealing drugs and combinations thereof.

As used herein, the term "pulse release" generally refers to a release profile of a drug that features a sudden surge of the release rate of the drug. The release rate surge of the drug would then disappear within a period. A more detailed definition of the term can be found in Encyclopedia of Controlled Drug Delivery, Edith Mathiowitz, Ed., Culinary and Hospitality Industry Publications Services.

In some embodiments, the term "fast release" refers to a release profile of a drug that features a release rate in the range between about 15 µg and about 40 µg per day (typically for one to three days) (or between about 45 µg and about 120 µg in three days) for a 18 mm stent, about 10 µg to about 27 µg per day (typically for one to three days) for a 13 mm stent, and about 6 (6.7) µg to about 17.2 µg per day (typically for one to three days) for a 8 mm stent. Equivalent profiles can be derived by one having ordinary skill in the art for stents having other sizes. The term "fast release" is used interchangeably with the term "burst release."

As used herein, the term "sustained release" generally refers to a release profile of a drug that can include zero-order release, exponential decay, step-function release or other release profiles that carry over a period of time, for example, ranging from several days to several weeks or years. The terms "zero-order release", "exponential decay" and "step-function release" as well as other sustained release profiles are well known in the art (see, for example, Encyclopedia of Controlled Drug Delivery, Edith Mathiowitz, Ed., Culinary and Hospitality Industry Publications Services). In some embodiments, sustained release refers to 2 to 15 µg per day for a selected number of days or weeks.

In another embodiment, the coating may include two or more drugs. One of the drugs or both drugs can have any one or combination of the pulsed, burst or sustained delivery profile. The coating can have a delivery profile that features a burst delivery of one or more drugs together with a sustained delivery of the one or more drugs. In one embodiment, the coating can be made to have a profile of a burst release of a first drug and sustained release of the first drug and a second drug. Alternatively, the coating can be made to have a burst release of a first and a second drug followed by a sustained release of the first and the second drug. The release rate of the drugs can be tailored by coating concentration of a drug and the equilibrium water uptake of the barrier if the barrier is formed of a hydrophobic, nonabsorable polymer or the absorption rate if the barrier is formed of an absorbable polymer.

For example, the coating can have a burst release in the first three days after implantation of an immunosuppressant, followed by a sustained release of the immunosuppresant thereafter or a sustained release of an anti-inflammatory drug or an antiplatelet drug over a period of two months.

In another embodiment of the present invention, a coating can be made to provide a release profile that includes a pulse release of one or more drugs and optionally a sustained release of the same or different drugs. The art of formulation to provide a pulsed release profile is well developed (see, for example, Encyclopedia of Controlled Drug Delivery, Edith Mathiowitz, Ed., Culinary and Hospitality Industry Publications Services). In one example, the upper most stent coating or surface thereof can be concentrated with the drug. In another example, a drug can be encapsulated within microcapsules. The degradation of the microcapsule wall can generate a pulsed release of the drug.

In one embodiment, a coating providing a pulse release profile can be made from nano or microparticulate drug loaded particles (DrugP) formed of a drug encapsulated within a degradable polymer. The drugP can be nanoparticles or microparticles of the drugP having a size ranging for example, from about 0.5 nm to about 1000 nm, or from about 1 µm to about 100 µm. Representative drug particles can have a size of about 0.5 nm, about 2 nm, about 5 nm, about 10 nm, about 20 nm, about 50 nm, about 75 nm, about 100 nm, about 200 nm, about 500 nm, about 750 nm, about 1000 nm, about 2 µm, about 5 µm, about 10 µm, about 20 µm, about 50 µm, about 75 µm, or about 100 µm.

The drugs forming the drugP can be any one or more bioactive agents described below. Representative drugs can be anti-proliferative everolimus, estradiol (e.g., 17-beta-estradiol), other estrogen receptors, anti-proliferative drugs, immunosuppresant drugs, anti-inflammatory drugs, anti platelet drugs, antimigratory drugs, anti-thrombotic drugs, agents that promotes endothelial cell growth, drugs that regress plaque such as high density lipoprotein (HDL)-mimetics, prohealing drugs and combinations thereof. The encapsulating polymer can be any degradable biocompatible polymer having a range of hydrolysis rate. Representative polymers include, but are not limited to, poly(glycolic acid) (PGA), poly(D,L-lactic acid) (DLPLA), polyhydroxyalkanoates (PHA), poly(ester amides) (PEA), and polyether esters such as poly(butylene terephthalate)/poly(ethylene glycol) (PBT/PEG). The drugP can be formed by emulsion methods known in the art (see, for example, Hans Mollet, Formulation Technology: Emulsions, Suspensions, Solid Forms, Wiley-VCH, 2001). The drugP can be suspended in a solution of a polymer and optionally the drug forming the drugP particles and then sprayed on the stent. Hydrolysis of the encapsulating polymer will allow the drug to be released from the drugP. The drugP having a size ranging from about 0.5 nm to 2 nm or from about 1 µm to 4 µm would favor surface degradation over bulk degradation. A population distribution of drugP can result in the drug release in the coating matrix at times that appear as a pulsed dosing from the coating matrix impressed on a background release of the same drug or a different drug if a drug is optionally included in the coating solution in which the drugP is suspended. The background release can be the same drug, a different drug or no drug at all. The background release of drug can be tailored to have a different profile as well. In one embodiment, the background release is sustained release.

In a further aspect of the present invention, the coating can be made to simultaneously release an agent that reduces smooth muscle cell migration and/or proliferation and an agent that promotes endothelial cell growth. Simultaneous delivery means that there is at least some overlap in the release of the drug. Under this embodiment, at least one of the drugs can be released first such as by pulsed, burst, or sustained delivery so long as there is an overlap in delivery with the second drug. Smooth muscle cell proliferation has been identified as a cause of restenosis, and endothelial cell growth contributes to vessel healing (see, for example, Chandrasekar, et al., J. Am. Coll. Cardiol. 38: 1570-6 (2001)). A combination of an anti-proliferative agent and an agent that promotes endothelial cell growth allows one to treat restenosis through different channels and may have a synergistic effect on ameliorating restenosis.

Coatings capable of simultaneously releasing an anti-proliferative agent and an agent that promotes endothelial cell growth can have a variety of configurations. For example, the coating can have a layer that comprises a mixture of the two agents or have two layers, each of which comprises a polymer and either the anti-proliferative agent or the agent that promotes endothelial cell growth.

In one embodiment, a composition containing a drug such as drugP particles described above can be formed from a polymer and one of the anti-proliferative agent and the agent that promotes endothelial cell growth. The composition such as the drugP particles can be suspended in a solution of the polymer and the other agent of the anti-proliferative agent or the agent that promotes endothelial cell growth and then coated on to a stent. The resultant coating would provide a pulsed release of one agent and a background release of the other agent.

The ani-proliferative agent useful for forming the various formulations described herein includes any anti-proliferative agents that reduce smooth muscle cell migration and/or proliferation. In one embodiment, the ani-proliferative agent is rapamycin, rapamycin derivatives, paclitaxel, docetaxel, 40-O-(3-hydroxy) propyl-rapamycin, 40-O-[2-(2-hydroxy) ethoxy]ethyl-rapamycin, and 40-O-tetrazole -rapamycin, ABT-578, everolimus and combinations thereof.

The agent that promotes endothelial cell growth useful for forming the various formulations described herein can be any agent that provides beneficial effect on endothelial cell growth. Exemplary agents promoting endothelial cell growth include, for example, vascular endothelial growth factor (VEGF), estradiol such as 17-beta-estradiol, agents that do not inhibit endothelial cell growth, and combinations thereof. Preferably, the endothelial cell growth promoting agent is estradiol, more preferably 17-beta-estradiol.

In one embodiment, the ani-proliferative agent is everolimus and the endothelial cell growth promoting agent is 17-beta-estradiol, and the simultaneous release of everolimus and 17-beta-estradiol can be achieved by three-layer coating on a stent. The first layer can be only a primer layer, the second layer can include a blend of everolimus and a polymer such as an EVAL polymer, and the third layer can have a blend of 17-beta-estradiol and a polymer such as an EVAL polymer.

In a further embodiment, a coating can be formed to include (1) a first drug that can be one of rapamycin, rapamycine derivatives, paclitaxel, docetaxel, 40-O-(3-hydroxy)propyl-rapamycin, 40-O-[2-(2-hydroxy)ethoxy]ethyl-rapamycin, and 40-O-tetrazole -rapamycin, ABT-578, everolimus and combinations thereof, (2) a second drug that can be one of vascular endothelial growth factor (VEGF), estradiol such as 17-beta-estradiol, agents that do not inhibit endothelial cell growth, and combinations thereof. The first and second drugs can have any of the aforementioned release profiles such as the first drug can have a pulse, burst and/or sustained release profile, and the second drug can have a pulse, burst and/or sustained release profile. The first drug can have a burst release followed by sustained release while the second drug has a sustained release. Alternatively, the second drug can have a burst release followed by sustained release while the first drug has a sustained release. Preferably, the first drug is everolimus and the second drug is 17-beta-estradiol.

The coating can have different constructs. For example, the coating can have a first layer that comprises a first drug and a first polymer, and a second layer that comprises a second drug and a second polymer. The first polymer and the second polymer can be same or different. In addition, the first layer and the second layer can have a drug/polymer ratio between 1/99 and 99/1, e.g., a ratio between 10/90 and 90/10.

Figure 2:
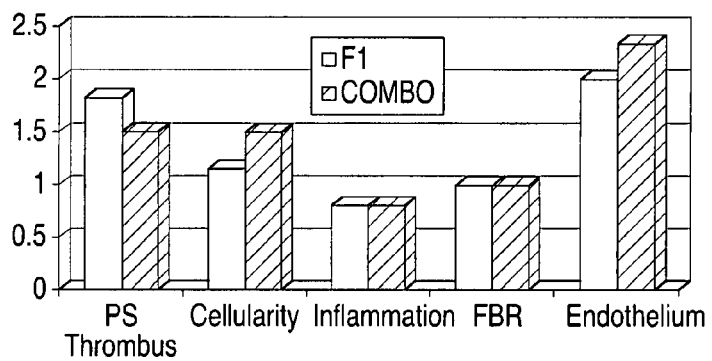
FIG. 2 shows the comparative vascular response of the two systems, the F1 and the Combo systems, at 14 days post implant, based on analysis of histology slides.

FIGS. 1 and 2 show an embodiment of the coatings described herein, which allows simultaneous release of both everolimus and 17-beta-estradiol. FIG. 1 shows porcine in vivo release profile of everolimus and 17-beta-estradiol in which "Combo" describes the stents that simultaneously release everolimus and 17-beta-estradiol and "F1" describes the stents that release only everolimus. The Combo stents include an EVAL primer layer and a layer of mixture of 1:3 everolimus to EVAL polymer ratio (total solid 284 µg) under a layer of mixture of 1:3 17-beta-estradiol to EVAL polymer ratio (total solid 372 µg). The F1 stents include an EVAL primer layer under a layer of a mixture of 1:3 everolimus to EVAL polymer ratio (total solid 284 µg). Vascular responses to the implants of F1 and Combo stents are shown in FIG. 2, which shows that the stent that simultaneously releases everolimus and 17-beta-estradiol can result in lower chances of peristrut thrombosis and higher chances of re-endothelialization as compared to the stent that releases only everolimus. Foreign body response (FBR) and inflammation were generally the same.

Figure 3:
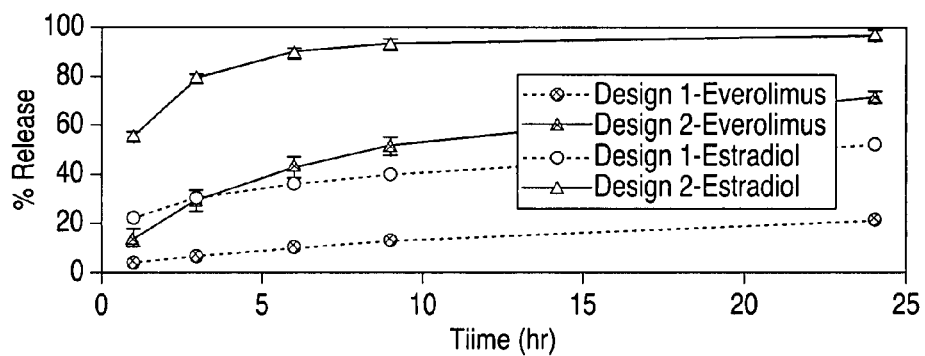
FIG. 3 shows the simultaneous release of everolimus and 17-beta-estradiol in phosphate-buffered saline (PBS)/Triton™ solution (polyoxyethylene octyl phenyl ether) (SPI Supplies, West Chester, Pa.).

FIG. 3 shows another embodiment of the present invention, which is simultaneous fractional release of everolimus and 17-beta-estradiol in Solef™ in phosphate-buffered saline (PBS)/Triton™ solution (polyoxyethylene octyl phenyl ether) (SPI Supplies, West Chester, Pa.). The stents have a PBMA primer layer and a layer of everolimus in PVDF under a layer of 17-beta-estradiol in PVDF. The designation of "Design 1" and that of "Design 2" in FIG. 3 correspond to two different stents of the same configuration with different polymer/drug ratios.

The coatings described above can be designed to have a topcoat or a finish coat that is capable of promoting accelerated-healing. This topcoat or finish coat can be made non-inflammatory and/or non-fouling. Non-inflammatory is defined as preventing inflammation or reducing inflammation to an acceptable degree. Non-fouling or anti-fouling is defined as preventing, delaying or reducing the amount of formation of protein build-up caused by the body's reaction to foreign material. The topcoat or finish coat can be combined with a tailored release of a drug or drugs at the finalcoat and/or the drug reservoir layers to further modulate the plaque stabilization and controlled healing. The accelerated-healing topcoat can be formed of one of polyester amide, Silk-elastin, elastin-epitoped supramolecular assembly of peptide amiphile or combinations thereof. The accelerated-healing topcoat can be made non-inflammatory, non-fouling by including a non-inflammatory, non-fouling material such as PolyActive™, PEG, hyaluronic acid and its derivatives, and heparin and its derivatives that can be a fragment heparin such as pentasaccharide, a derivative heparin or a complexed heparin. Heparin derivatives can be any functional or structural variation of heparin. Representative variations include alkali metal or alkaline—earth metal salts of heparin, such as sodium heparin (e.g., hepsal or pularin), potassium heparin (e.g., clarin), lithium heparin, calcium heparin (e.g., calciparine), magnesium heparin (e.g., cutheparine), low molecular weight heparin (e.g., ardeparin sodium) with a molecular weight of from about 4,000 to about 5,000 Daltons and high affinity heparin (see, e.g., Scully, et al., Biochem. J. 262:651-658 (1989)). Other examples include heparin sulfate, heparinoids, heparin based compounds and heparin having a hydrophobic counter-ion such as tridodecylmethylammonium and benzalkonium.

The coatings described herein can optionally have one or more bioactive agents, which may be the same or different from the drugs described in the above. Examples of such agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Other examples of drugs include antibodies, receptor ligands, and enzymes, adhesion peptides, oligosaccharides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Such agents can also include a prohealing drug that imparts a benign neointimal response characterized by controlled proliferation of smooth muscle cells and controlled deposition of extracellular matrix with complete luminal coverage by phenotypically functional (similar to uninjured, healthy intima) and morphologically normal (similar to uninjured, healthy intima) endothelial cells. Such agents can also fall under the genus of antineoplastic, cytostatic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include heparinoids, hirudin, recombinant hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, antibody, and thrombin inhibitors such as Angiomax ä (Biogen, Inc., Cambridge, Mass.). Examples of cytostatic agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Other drugs include calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon, genetically engineered epithelial cells, antibodies such as CD-34 antibody, abciximab (REOPRO), and progenitor cell capturing antibody, prohealing drugs that promotes controlled proliferation of muscle cells with a normal and physiologically benign composition and synthesis products, enzymes, anti-inflammatory agents, antivirals, anticancer drugs, anticoagulant agents, free radical scavengers, steroidal anti-inflammatory agents, non-steroidal anti-inflammatory agents, antibiotics, nitric oxide donors, super oxide dismutases, super oxide dismutases mimics, 4-amino-2,2,6,6-tetramethylpiperidine-1-oxyl(4-amino-TEMPO), dexamethasone, clobetasol, aspirin, pro-drugs thereof, co-drugs thereof, and a combination thereof. The foregoing substances are listed by way of example and are not meant to be limiting. Other active agents which are currently available or that may be developed in the future are equally applicable.

The stent coating formulation provided herein can include any biocompatible polymer. Representative examples of polymers that can be used to coat an implantable device in accordance with the present invention include, but are not limited to, poly(ester amide), polyhydroxyalkanoates (PHA) such as poly(3-hydroxyalkanoates), e.g., poly(3-hydroxypropanoate), poly(3-hydroxybutyrate), poly(3-hydroxyvalerate), poly(3-hydroxyhexanoate), poly(3-hydroxyheptanoate) or poly(3-hydroxyoctanoate), poly(4-hydroxyalknaote), e.g., poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, polyesters, poly(D,L-lactide), poly (L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly (tyrosine carbonates) and derivatives thereof, poly(tyrosine ester) and derivatives thereof, poly(imino carbonates), poly (glycolic acid-co-trimethylene carbonate), polyphosphoester, polyphosphoester urethane, poly(amino acids), polycyanoacrylates, poly(trimethylene carbonate), poly (iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as vinylidene fluoride based homopolymer (PVDF) and copolymers such as poly(vinylidene fluoride-co-hexafluoropropylene) (PVDF-HFP) known as Solef™ or Kynar™ polymers and polyvinylidene chloride, polyfluoroalkenes such as tetrafluoroethylene (Teflon™), polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether esters) (e.g. PEO/PLA); polyalkylene oxides such as poly(ethylene oxide), poly(propylene oxide), polyalkylene oxalates, polyphosphazenes, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly (methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, starch, collagen, dextran, dextrin, fragments and derivatives of hyaluronic acid, heparin, fragments and derivatives of heparin, glycosamino glycan (GAG), GAG derivatives, polysaccharide, elastin, alginate, and combinations thereof.

As used herein, the terms poly(D,L-lactide) (PDLL), poly (L-lactide) (PLL), poly(D,L-lactide-co-glycolide) (PDLLG), and poly(L-lactide-co-glycolide) (PLLG) are used interchangeably with the terms poly(D,L-lactic acid) (PDLLA), poly(L-lactic acid) (PLLA), poly(D,L-lactic acid-co-glycolic acid) (PDLLAGA), and poly(L-lactic acid-co-glycolic acid) (PLLAGA), respectively.

Although embodiments of local drug delivery has been described in reference to a stent (balloon or self expandable), other medical substrates that can be implanted in a human or veterinary patient are also applicable with the embodiments of the invention. Examples of such implantable devices include stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (EL-GILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data are not to be construed to unduly limit the scope of the embodiments of the invention.

Examples 1-2

Drug-Eluting Coatings having a Fast and Slow Release of Estradiol from 13 mm Penta™ Stents Penta™ stents (available from Guidant) can be coated according to the configurations defined in Table 1 to provide a fast release or a slow release of estradiol.

TABLE 1

Coating configurations of Penta ™ stents for delivery of estradiol

| | | Primer | | Reservoir | | | | Topcoat | | |
|---|---|---|---|---|---|---|---|---|---|---|
| | | | | | Drug | Solid | | | Topcoat | |
| | Release | Polymer | Primer | | Polymer | Content | Target | | Polymer | Target | |
| 1 | Fast | EVAL | 40 µg | A | EVAL | 300 µg | 600 mg | B | EVAL | 100 µg | C |
| 2 | Slow | EVAL | 40 µg | A | EVAL | 300 µg | 600 mg | B | PBMA | 40 µg | D |

A: 3% EVAL/72% DMAC/25% ethanol.
B: 2% EVAL/1% Estradiol/77% DMAC/20% pentane.
C: 4% EVAL/76% DMAC/20% pentane.
D: 1% PBMA/43% Techspray™/6% acetone/50% xylene.

Examples 3-4

Drug-Eluting Coatings having a Fast and Slow Release of Everolimus

Penta™ stents can be coated according to the configurations defined in Table 2 to provide a fast release or a slow release of everolimus.

TABLE 2

Coating configurations of Penta ™ stents for delivery of everolimus

| | | Primer | | | Reservoir | | | | Topcoat | | |
|---|---|---|---|---|---|---|---|---|---|---|---|
| | | | | | Drug | Solid | | | Topcoat | |
| | Release | Polymer | Primer | | Polymer | Content | Target | | Polymer | Target | |
| 3 | Fast | EVAL | 40 µg | A | EVAL | 385 mg | 615 µg | B | EVAL | 40 µg | C |
| 4 | Slow | EVAL | 40 µg | A | EVAL | 273 mg | 478 µg | B | PBMA | 189 µg | C |

A: 3% EVAL/72% DMAC/25% ethanol.
B: 2% EVAL/1% everolimus/77% DMAC/20% pentane.
C: 4% EVAL/76% DMAC/20% pentane

Example 5

Preclinical Study of Drug-Delivery Implants

The following preclinical data are representative results from the drug-eluting stent (DES) implants of everolimus and 17-beta-estradiol in a hypercholesterolemic rabbit model of human thin-cap fibroatheroma (TCFA). The MULTI-LINK Penta™ 13 mm was the platform for all DES and metallic stents. Both a slow release and fast release formulation of each drug were tested and the results were evaluated at 28 days. In both FIGS. 4 and 5, the test results concerning the slow release formulation were labeled with "s", the test results concerning the fast release formulation were labeled with "f", and the test results data concerning a formulation having both a slow and a fast release of an agent are labeled with "s+f."

Figure 4:
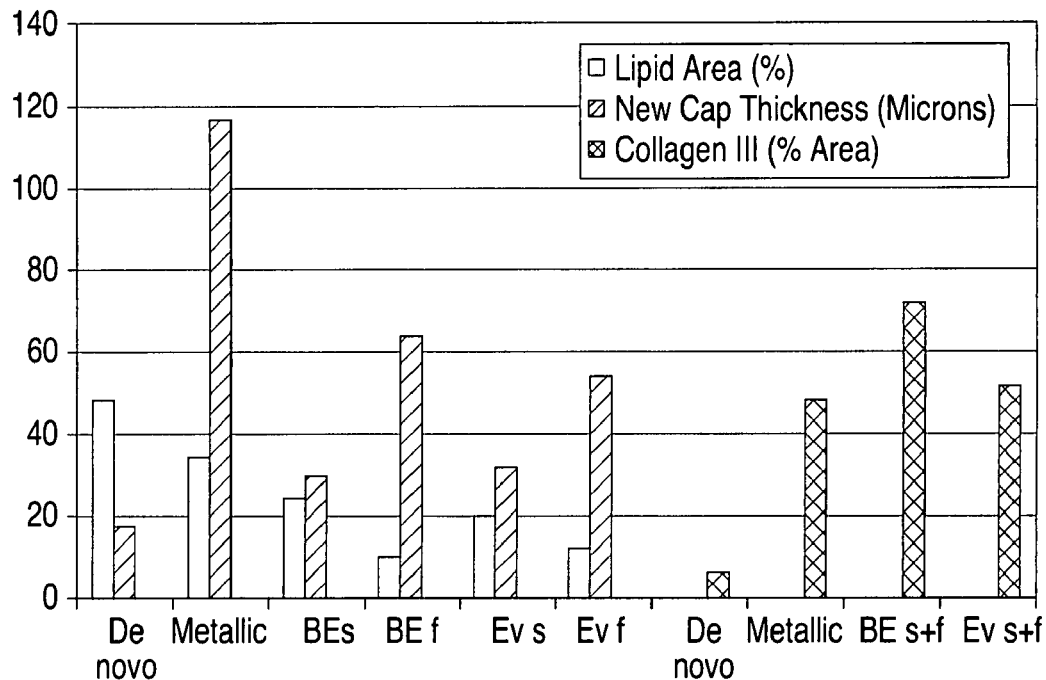
FIG. 4 shows the percent lipid area, total fibrous cap thickness, and collagen type III percent area for the thin-cap fibroatheromas stented as indicated in an experimental animal model of atherosclerosis.

As shown in FIG. 4, compared to the unstented (de novo) TCFAs, both formulations of beta estradiol reduced the percent lipid area and increased the total fibrous cap thickness. Compared to TCFAs treated with metallic stents, both formulations of beta estradiol reduced the percent lipid area and decreased the total fibrous cap thickness. The slow release formulation resulted in a smaller total fibrous cap thickness but with a larger percent lipid area compared to the fast release formulation. Compared to the metallic stents, both formulations of everolimus reduced the percent lipid area and decreased the total fibrous cap thickness. As with the beta-estradiol, the slow release formulation of everolimus yielded a smaller total fibrous cap thickness but with a larger percent lipid area compared to the fast release formulation. Together, these results illustrate that on de novo TCFAs, both beta-estradiol and everolimus drug-delivery stent reduce percent lipid area and increase total cap thickness. The increase in cap thickness in the drug-delivery stent arms was more controlled than the increase observed with the metallic stents. In particular, the slow release formulations may be effective at stabilizing TCFA by reducing percent lipid area while reducing the chance of restenosis as a result of the attenuated fibrous cap thickening. The increased expression of newer collagen type III suggests a reparative process post-stenting, such that the overall increase in interstitial collagen imparts increased structural integrity to the fibrous cap, thereby providing a possible mechanism for stabilizing the TCFA. In this respect, both drug-delivery stent arms were as effective as metallic stents in this animal model of atherosclerosis.

Figure 5:
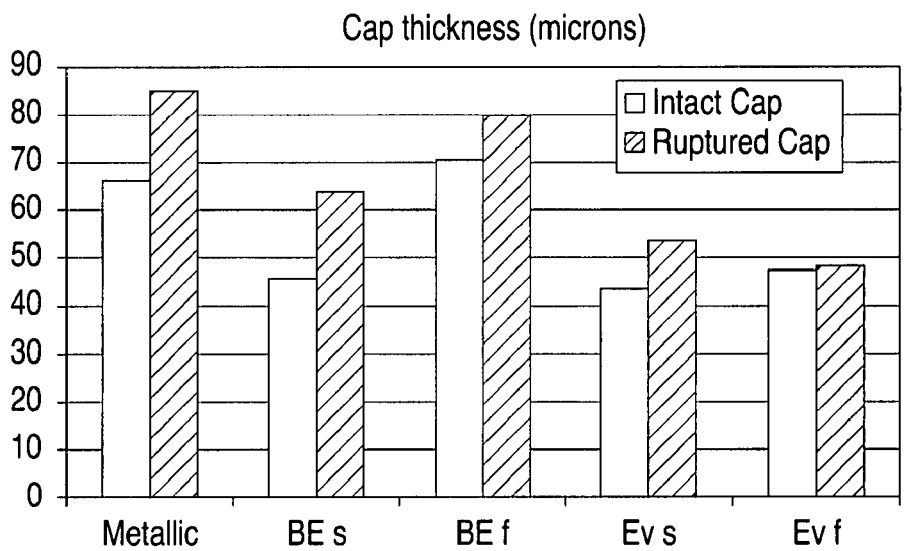
FIG. 5 shows the neointimal areas measured in cases of both fibrous cap rupture and intact fibrous cap for the thin-cap fibroatheromas stented as indicated in an experimental animal model of atherosclerosis.

FIG. 5 shows the neointimal areas measured in cases of both fibrous cap rupture and intact fibrous cap for all stent arms in this animal model. These preclinical results have clinical significance in that with current interventional devices and procedures, the fibrous cap is likely to be ruptured during stent deployment. In each stent arm, rupture of the fibrous cap (hatched areas) by stent struts resulted in increased neointimal formation as compared to sections where the fibrous cap remained intact (solid areas). This response of increased neointimal formation in the case of fibrous cap rupture was attenuated, but not completely eliminated, by drug-delivery stent at 28 days. The lowest neointimal areas were obtained in the everolimus arms. For the full range of intact and ruptured fibrous caps, the slow release everolimus yielded similar results as compared to the fast release everolimus.

Example 6

Simultaneous Release of Everolimus and 17-Beta-Estradiol

Onto Vision 12 mm small stents (available from Guidant) can be coated according to the following configurations. An auto coater can be used to coat the abluminal surface of the stent.

Configuration A

Drug coating: coating with 200 µg of poly(D,L-lactic acid) (PDLLA)/estradiol, from 4.8% poly(D,L-lactic acid) (PDLLA), 4.8% estradiol, and 90.4% acetone, by 3 passes, drying at 35° C. for 8 hours, and then coating with 200 µg of DL-PLA/everolimus, from 4.8% DL-PLA, 4.8% everolimus, and 90.4% acetone, coating by 3 passes, drying at 35 ° C. for 8 hours.

Configuration B

Primer: coating with 80 µg PDLLA, using one pass coating, from 9.6% DL-PLA in acetone solution, baking at 120° C. for 1 hr; and Drug coating: coating with 200 µg of PDLLA/estradiol, from 4.8% PDLLA, 4.8% estradiol, and 90.4% acetone, by 3 passes, drying at 35 ° C. for 8 hours, and then coating with 200 µg of PDLLA/everolimus, from 4.8% PDLLA, 4.8% everolimus, and 90.4% acetone, by 3 passes, drying at 35° C. for 8 hours.

Configuration C

Primer: coating with 80 µg PDLLA, using one pass coating, from 9.6% PDLLA in acetone solution, baking at 120° C. for 1 hr;

Drug: coating with 200 µg of estradiol, from 5% estradiol solution in acetone, using 3 pass coating;

Inter coat: coating with 80 µg PDLLA, using one pass coating, from 9.6% PDLLA in acetone solution, baking at 35° C. for 1 hr; and Drug coat: coating with 200 µg of PDLLA/everolimus, from 4.8% PDLLA, 4.8% everolimus, and 90.4% acetone, by 3 passes, drying at 35 ° C. for 8 hours.

Configuration D

Primer: coated with 80 µg PDLLA, using one pass coating, from 9.6% PDLLA in acetone solution, baking at 120° C. for 1 hr;

PDLLA /drug: coating with 300 µg of PDLLA /estradiol, from 4.8% PDLLA, 4.8% estradiol, and 90.4% acetone, by 4 passes, drying at 35° C. for 8 hours;

Pure everolimus: coating with 100 µg everolimus, from 10% drug solution in MEK (methylethylketone), by 2 passes, baking at 50° C. for 1 hr; and Top coat: coating with 100 µg Polyactive™, using one pass coating, from a 5% solution of 5% Polyactive™, 76% chloroform, and 19% 1,1,2-trichloroethane.

Configuration E

Primer: coating with 80 µg PDLLA, using one pass coating, from 9.6% PDLLA in acetone solution, and baking at 120° C. for 1 hr;

Poly(ester amide) (PEA)/estradiol: coating with 200 µg of PEA/estradiol, from 5% PEA, 5% estradiol, 72% chloroform, and 18% 1,1,2-trichloroethane, by 3 passes, drying at 35° C. for 8 hours;

PEA/everolimus: coating with 200 µg of PEA/everolimus, from a solution that includes 5% PEA, 5% everolimus, 72% chloroform, and 18% 1,1,2-trichloroethane, by 3 passes, and drying at 35° C. for 8 hours; and Top coat: coating with 100 µg Polyactive™, using one pass coating, from a 5% solution of 5% PolyactiveTM in 76% chloroform, and 19% 1,1,2-trichloroethane.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A drug delivery stent, comprising:
a primer;
a reservoir layer comprising estradiol;
an intercoat;
a second reservoir layer comprising everolimus encapsulated in nano- and/or micro- particles and unencapsulated everolimus.

2. The drug delivery stent of claim 1, wherein the estradiol is 17-beta-estradiol.

3. The drug delivery stent of claim 1, wherein the stent is capable of:
burst and/or pulsed and sustained release of everolimus; and
sustained release of estradiol.

4. The drug delivery stent of claim 1, wherein the first drug reservoir layer and/or the second drug reservoir layer further comprise a polymer wherein the polymer may be the same or different in each layer.

5. The drug delivery stent of claim 4, wherein the first and second polymers are independently selected from the group consisting of poly(ethylene vinyl alcohol) (EVAL), poly(D, L-lactic acid) (PDLLA), poly(ester amide) (PEA), polybutylmethacrylate (PBMA), poly(ether ester), and poly(vinylidene fluoride) (PVDF).

6. A method of treating a disorder in a patient comprising implanting in the patient the stent of claim 1, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor, and combinations thereof.

7. The method of claim 6, wherein:
the everolimus is released from an 18 mm stent at a rate of about 15 µg to about 40 µg per day for at least one day after implantation.

8. The method of claim 7, wherein the everolimus is released from the stent at a rate of about 15 µg to about 40 µg per day for one to three days after implantation.

9. The method of claim 6, wherein:
the everolimus is released from a 13 mm stent at a rate of about 10 µg to about 27 µg per day for at least one day after implantation.

10. The method of claim 6, wherein:
the everolimus is released from an 8 mm stent at a rate of about 6 µg to about 17.2 µg per day for at least one day after implantation.

\* \* \* \* \*